(12) United States Patent
Mawatari et al.

(10) Patent No.: US 11,577,006 B2
(45) Date of Patent: *Feb. 14, 2023

(54) BIOIMPLANT

(71) Applicants: SAGA UNIVERSITY, Saga (JP); KYOCERA Medical Corporation, Osaka (JP)

(72) Inventors: Masaaki Mawatari, Saga (JP); Masatsugu Tsukamoto, Saga (JP); Iwao Noda, Osaka (JP)

(73) Assignees: KYOCERA CORPORATION, Kyoto (JP); SAGA UNIVERSITY, Saga (JP)

( * ) Notice: Subject to any disclaimer, the term of this patent is extended or adjusted under 35 U.S.C. 154(b) by 37 days.

This patent is subject to a terminal disclaimer.

(21) Appl. No.: 17/080,460

(22) Filed: Oct. 26, 2020

(65) Prior Publication Data

US 2021/0052780 A1     Feb. 25, 2021

Related U.S. Application Data

(63) Continuation of application No. 15/405,156, filed on Jan. 12, 2017, now Pat. No. 10,814,039, which is a continuation-in-part of application No. 14/376,183, filed as application No. PCT/JP2013/050661 on Jan. 16, 2013, now abandoned.

(30) Foreign Application Priority Data

Feb. 3, 2012   (JP) ................ 2012-022205

(51) Int. Cl.
  *A61L 27/32*   (2006.01)
  *A61L 27/54*   (2006.01)

(52) U.S. Cl.
  CPC ........... *A61L 27/54* (2013.01); *A61L 27/32* (2013.01); *A61L 2300/104* (2013.01); *A61L 2300/404* (2013.01); *A61L 2420/02* (2013.01)

(58) Field of Classification Search
  CPC ......... A61L 2300/104; A61L 2300/404; A61L 2420/02; A61L 27/32; A61L 27/54
  See application file for complete search history.

(56) References Cited

U.S. PATENT DOCUMENTS

| 5,482,731 A | 1/1996 | Vargas-Gutierrez |
| 6,426,114 B1 | 7/2002 | Troczynski |
| (Continued) | | |

FOREIGN PATENT DOCUMENTS

| JP | 2005-506879 A | 3/2005 |
| JP | 2008-073098 A | 4/2008 |
| (Continued) | | |

OTHER PUBLICATIONS

Gross et al. (J Mater Sci. 1998;33:3985-3991). (Year: 1998).*

(Continued)

*Primary Examiner* — Ernst V Arnold
(74) *Attorney, Agent, or Firm* — Duane Morris LLP

(57) ABSTRACT

Provided is a bioimplant which is capable to inhibit the biofilm formation over a long period of time after an operation. The bioimplant of the present invention comprises a base material of metal, ceramic, or plastic and a thermal spraying film of a calcium phosphate-based material formed at least partially thereon and the silver concentration in the thermal-spray film is 0.05 wt % to 3.00 wt %.

5 Claims, 1 Drawing Sheet

(56) References Cited

U.S. PATENT DOCUMENTS

| | | | |
|---|---|---|---|
| 10,004,604 B2 | 6/2018 | Hotokebuchi | |
| 10,610,614 B2* | 4/2020 | Hotokebuchi | ........ A61L 27/425 |
| 10,814,039 B2* | 10/2020 | Mawatari | ................ A61L 27/32 |
| 11,278,642 B2* | 3/2022 | Hotokebuchi | .......... A61L 27/54 |
| 2009/0280156 A1 | 11/2009 | Hotokebuchi et al. | |
| 2010/0286790 A1 | 11/2010 | Gruner et al. | |
| 2011/0008407 A1 | 1/2011 | Gan et al. | |
| 2013/0138223 A1 | 5/2013 | Mawatari et al. | |
| 2015/0018965 A1* | 1/2015 | Mawatari | ................ A61L 27/32 |
| | | | 623/23.61 |

FOREIGN PATENT DOCUMENTS

| | | |
|---|---|---|
| JP | 2011-512959 A | 4/2011 |
| WO | 03/035123 A1 | 5/2003 |
| WO | 2008/029612 A1 | 3/2008 |
| WO | 2009/111307 A2 | 11/2009 |
| WO | 2012/023510 A1 | 2/2012 |

OTHER PUBLICATIONS

Bai etBai et al. (J Biomed Mater Res Part B. 2012;100B:553-561) (Year: 2012).*

Estridge and Reynolds. Basic Clinical Laboratory Techniques 2011; p. 111 (2 pages). (Year: 2011).

Lee, M.S., Reference Book for Composites Technology vol. 2 1989, CRC Press; p. 82 (Year: 1989).

Ong et al. Critical REviews in Biomedical Engineering 1999;28(5 &6): 1-41 (Year: 1999).

Chai (Dr. Cameron Chai, Hydroxyapatite—Thermal Stability of Synthetic Hydroxyapatites, (Jun. 2002), [Retrieved from internet < URL: . https://www.azom.com/article.aspx?Article1D=1462 >], 3 pages) (continued below as ref. 5) (Year: 2002).

Chai et al. (continued from ref. 4, above) Hydroxyapatite—Thermal Stability of Synthetic Hydroxyapatites (2002) (Source: International Ceramic Monographs, vol. 1, No. 1, pp. 79-85 (1994)) (Year: 2002).

Gross et al., Oxyapatite in hydroxyapatite coatings, Journal of Materials Science, (1998), 33: 3985-3991 (Year: 1998).

Extended European Search Report dated Aug. 6, 2015 in counterpart European Patent Application No. 13743971.7, 7 pages.

International Search Report dated Feb. 4, 2013, in counterpart Japanese Patent Application No. PCT/JP2013/050661, 2 pages (English translation).

International Preliminary Report on Patentability dated Aug. 5, 2014, in counterpart Japanese Patent Application No. PCT/JP2013/050661, 6 pages (English translation).

Noda, et al., "Development of Novel Thermal Sprayed Antibacterial Coating and Evaluation of Release Properties of Silver Ions", Journal of Biomedical Materials Research, Part B: Applied Biomaterials, May 2009, 89(2):456-65 (PubMed, DOI:10.1002/jbm.b.31235).

Shimizaki et al., "In vivo antibacterial and silver-releasing properties of novel thermal sprayed silver-containing hydroxyapatite coating", Journal of Biomedical Materials Research Part B: Applied Biomaterials, 2009, pp. 386-389.

Ando et al., "Development of antibacterial biomaterials", Orthopaedic Surgery and Traumatology, Apr. 2010, 53 (5):467-475 (Partial English Translation).

Miyamoto et al, "Development of novel antibacterial biomaterials", Antibiotics & Chemotherapy, 2010, 26(9):125-129 (Partial English Translation).

Noda et al., "Silver-containing hydroxyapatite coating", Journal of Japanese Society for Biomaterials, 2010, 29-4:266-270 (Partial English Translation).

Noda et al., "Development of Thermal Spraying Technique for Silver-Containing Hydroxyapatite (The 4th Report)", The 40th Annual Meeting of the Japanese Society for Replacement Arthroplasty Program/Abstract, 2010, p. 350 (Partial English Translation).

Noda et al., "Development of Thermal Spraying Technique for Silver-Containing Hydroxyapatite (The 5th Report)", The 41st Annual Meeting of the Japanese Society for Replacement Arthroplasty Program/Abstract, 2011, p. 371 (Partial English Translation).

Ando et al., "Development of Silver Antibacterial Biomaterials", The 34th Annual Meeting of the Japanese Society for Study of Bone and Joint Infection Program/Abstract, 2011, p. 64 (Partial English Translation).

* cited by examiner

BIOIMPLANT

RELATED APPLICATIONS

This application is a continuation application of U.S. application Ser. No. 15/405,156, filed Jan. 12, 2017, which is a continuation-in-part of U.S. application Ser. No. 14/376,183 entitled "Bioimplant" filed on Aug. 1, 2014, the content of which is incorporated herein in its entirety.

BACKGROUND OF THE INVENTION

The present invention relates to an antimicrobial bioimplant.

SUMMARY OF THE INVENTION

Use of bioimplants for treatment of bone injuries/diseases is steadily increasing along with expansion of active and elderly populations. For use as a bone substitute for broken or removed bones or for use as a support to assist a weakened bone, the synthetic bone substitute should form a strong joint or bone together with natural bones and assure the structural integrity thereof. A bone can grow into a neighboring tissue, especially when it is a porous tissue similar to the bone. However, in addition to the growth into porous tissue, the natural bone thus grown into the porous tissue should bind to the bioimplant, forming strong adhesion between them.

An important requirement for fixation of a bioimplant to bone is that the bone grows on and/or into the surface of the bioimplant. Various studies disclose that a calcium phosphate coating on an implant made of cobalt-chromium (Co—Cr) or a titanium (Ti) alloy, for example, a biologic apatite accelerates bone adhesion more quickly than if the implant made of the alloy has a non-coated surface. The biologic apatite $Ca_{10}(PO_4)_6(OH)_2$ is one of the main compounds which constitute human bone and teeth. The synthesized hydroxyapatite (HA) closely resembles a natural apatite and thus has been used in a study in which HA is used in dental and orthopedic implants. An implant has been produced which is easily integrated with neighboring bones and tissues by coating with HA or other crystalline calcium phosphates after transplantation.

However, although use of the synthetic joints in orthopedics for treatment of degenerative joint diseases is a therapeutic treatment effective for reconstruction of joint function, microbes may proliferate on the surface of the synthetic joints, causing post-operative infection. It is because microbes can adhere to the surface of the synthetic joint and the adhered microbes can form a habitat called biofilm. In such a case, antimicrobial agents (antibiotics) are not effective any more, making it difficult to treat the infection. Moreover if myelitis occurs, it is necessary to remove the synthetic joint and repeat the surgery and there may be possibly a case where the infected limb should be ablated.

However, although use of the synthetic joints in orthopedics for treatment of degenerative joint diseases is a therapeutic treatment effective for reconstruction of joint function, microbes may proliferate on the surface of the synthetic joints, causing post-operative infection. It is because microbes can adhere to the surface of the synthetic joint and the adhered microbes can form a habitat called biofilm. In such a case, antimicrobial agents (antibiotics) are not effective any more, making it difficult to treat the infection. Moreover if myelitis occurs, it is necessary to remove the synthetic joint and repeat the surgery and there may be possibly a case where the infected limb should be ablated.

Therefore, there are proposed a method of coating a hydroxyapatite film having high crystallinity and large specific surface area, which is suited for impregnation with an antibiotic, by precipitating hydroxyapatite on the surface of an implant and drying the hydroxyapatite, and a therapeutic agent-impregnated implant in which the coating film is impregnated with the antibiotic (Patent Document 1). The bioimplant prepared by the method is suited for impregnation of antibiotics. However, since the coating film has uniform pore size and porosity, it is difficult to perform sustained release of a medicine at a desired rate and thus the medicine tends to be eluted at a fixed rate at a time.

Alternatively, the applicant proposed a method of controlling the rate of releasing an antibacterial or antimicrobial agent by adjusting the evanescence speed of HA by adjusting the crystallinity of the coating layer of calcium phosphate-based material (Patent Document 2)

PATENT DOCUMENTS

[Patent Document 1] JP-A No. 2005-506879; [Patent Document 2] JP-A No. 2008-73098

DETAILED DESCRIPTION OF THE PREFERRED EMBODIMENTS

Technical Problems to be Solved

Figure 1A:
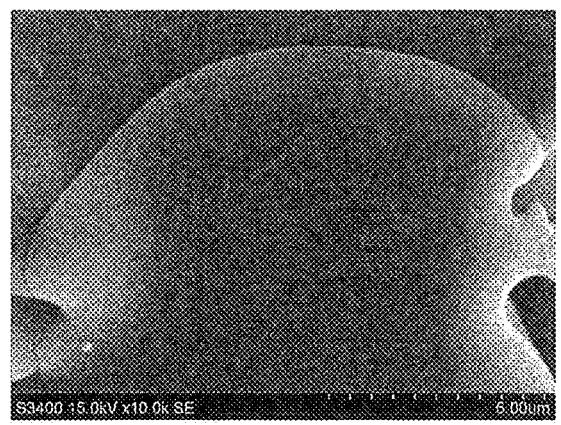
FIG. 1A shows an scanning electron microscope (SEM) image of a surface of the spray coating without carrying out the hydration-treatment.

As described in the above, one of the reasons of post-operative infection is that the microbes form the biofilm on the surface of the implant and this causes the antimicrobial agents to be not effective. Especially, for 24 hours after operation, a risk of the microbial infection is significantly high, because the immune function of a patient is significantly weakened. After that period, the patient slowly recovers own immune function. However, a highly possible state of microbial infection continues over a long period ranging from one week to several weeks after an operation. Especially, a patient having autoimmune disease such as diabetes and further having a weak resistance to the microbial infection (compromised host) has a high risk of microbial infection. Further, a patient who develops infection after implant operation has high infection rates ranging from several times to several tens times in comparison with normal case, when having an operation of replacing implant. Thus, a bioimplant which is capable to inhibit the biofilm formation over a long period of time after an operation is needed. However, it was difficult for the conventional bioimplant to be capable to inhibit the biofilm formation over such a long period of time.

Thus, an object of the present invention is to provide a bioimplant which is capable to inhibit the biofilm formation over a long period of time after an operation.

Means to Solve the Problems

The bioimplant according to the present invention, which was made to overcome the problems above, is characterized in that it comprises a base material of metal, ceramic or plastic and a thermal spraying film made of a calcium phosphate-based material formed at least partially thereon, the silver concentration in the thermal spraying film being 0.05 wt % to 3.00 wt %.

In the present invention, the calcium phosphate-based material is preferably a compound or a mixture of two or more compounds selected from the group consisting of hydroxyapatite, α-tricalcium phosphate, β-tricalcium phosphate, and tetracalcium phosphate.

Effect of the Invention

Since the bioimplant of the present invention can inhibit the biofilm formation over a long period of time after an operation, a curative effect of antimicrobial agents on infection can be maintained, and thereby decreasing risk of post-operative infection. Further, as used herein, "long period of time" refers to a period in which the risk of the post-operative infection is high, and the period ranges from one week to several weeks after an operation.

BEST MODE FOR CARRYING OUT THE INVENTION

Hereinafter, favorable embodiments of the present invention will be described in detail.

The bioimplant according to the present invention is a bioimplant, comprising a base material of metal, ceramic, or plastic and a thermal spraying film made of a calcium phosphate-based material formed at least partially thereon, the silver concentration in the thermal spraying film being 0.05 wt % to 3.00 wt %.

The bioimplant according to the present invention include metal, ceramic, and plastic implants, such as synthetic bones and fixation devices used for treatment of diseases and injuries, synthetic joints used for reconstruction of lost joint function, and synthetic tooth roots used for reconstruction of teeth.

A metal, ceramic, or plastic material may be used as the base material of the bioimplant. A stainless steel alloy, a cobalt-chromium alloy, titanium, a titanium alloy, alumina, zirconia or the like may be used as the metal, but titanium and titanium alloys are preferable. The titanium alloys for use include alloys of titanium with at least one metal selected from aluminum, tin, zirconium, molybdenum, nickel, palladium, tantalum, niobium, vanadium, platinum and the like. Preferably, it is Ti-6Al-4V alloy. Alternatively, the ceramics for use include, for example, alumina, zirconia, composite alumina-zirconia ceramics and the like. Yet alternatively, the plastics for use include, for example, polyethylenes, fluorine resins, epoxy resins, PEEK resins, Bakelite and the like.

The calcium phosphate-based material for use may be a compound or a mixture of two or more compounds selected from the group consisting of hydroxyapatite, α-tricalcium phosphate, β-tricalcium phosphate, and tetracalcium phosphate. It is preferably hydroxyapatite.

(Production Method)

The thermal spraying methods used for forming a thermal spraying film of a calcium phosphate-based material include flame spraying method, high-speed flame spraying method, plasma spraying method, and cold spraying method. For example in the case of the flame spraying method, a film is formed on the surface of a base material by melting a thermal spraying material or bringing it close to the melting state by placing it in a gas flame generated with oxygen and a flammable gas and spraying the resulting thermal spraying material on the base material. In the case of the normal flame spraying method, the thermal spraying temperature is about 2700° C. and the thermal spraying speed is Mach 0.6. Under normal thermal spraying condition, for example, a thermal spraying powder can be fed with 100 psi dry air into a gas frame torch generated with 50 psi oxygen gas and 43 psi acetylene gas and the resulting powder can be thermally sprayed at a thermal spraying distance of 60 to 100 mm.

The thickness of the thermal spraying film is 5 to 100 μm, preferably 20 to 40 μm, since it is not possible to cover the thermal spraying area entirely when the thickness is less than 5 μm and the adhesion strength of the film declines because of the residual stress during thermal spraying when the thickness is more than 100 μm.

It is preferable to carry out a heat-treatment of the prepared thermal spraying film. The heat-treatment can increase the crystallinity of a calcium phosphate-based material, and thereby improving the stability of the film. The heat-treatment may be carried out at a temperature range of 400 to 1000° C. for 0.5 to 7 hours under the reduced pressure of $10^{-2}$ Pa or less. It is preferable to carry out at a temperature range of 550 to 850° C. for 1 to 5 hours.

Figure 1B:
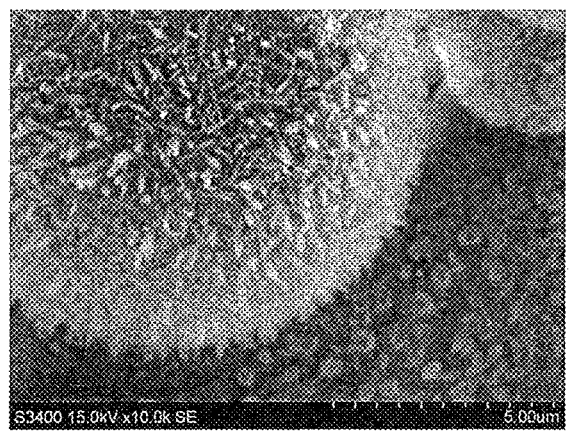
FIG. 1B shows an SEM image of the surface of a spray coating after carrying out the hydration-treatment.

Further, it is preferable to carry out a hydration-treatment of the prepared thermal spraying film after carrying out the heat-treatment. The hydration-treatment can convert oxyapatite to hydroxyapatite, and results in fine crystals of calcium phosphate being formed (e.g., separated out from the coating and/or deposited/precipitated) on the surface of the coating, thereby stabilizing an elution property of silver ion. As used herein, "separated out" refers to a process in which an insoluble crystalized material is exposed or separated, whereas a soluble material is dissolved. Also, as used herein, "deposited/precipitated" refers to a process in which new crystals are generated and accumulated on the surface of a coating. The formation of fine crystals of calcium phosphate on the surface of the coating stabilizes the elution property of silver ions because the fine crystals cover the surface of the coating, which reduces the rate of elution of silver ions. The hydration-treatment includes a step of adding water molecule to material and may be carried out, for example, by immersing the thermal spraying film in water at a temperature of 60-100° C. for 10-60 minutes, in accordance with some embodiments. FIG. 1A shows an scanning electron microscope (SEM) image of a surface of the spray coating without carrying out the hydration-treatment and FIG. 1B shows an SEM image of the surface of spray coating after carrying out the hydration-treatment. As shown in FIG. 1B, it is observed that needle-shaped crystals, plate-shaped crystals, and/or granular-shaped crystals are formed on the surface of the coating. In some embodiments, the size of the crystals in length, width or thickness is in the range of approximately 0.01 to 2.00 micrometers (μm).

It is possible to control the silver concentration in the thermal spraying film by adjusting the amount of the raw silver material blended to the thermal spraying material, i.e., the calcium phosphate-based material. The silver concentration in the thermal spraying film is 0.05 wt % to 3.00 wt %, preferably 0.05 wt % to 2.50 wt %, more preferably 0.05 wt % to 1.00 wt %, and more preferably 0.1 wt % to 1.00 wt %. It is because the antimicrobial action is not sufficient when the silver concentration is less than 0.05 wt %. Alternatively when it is more than 3.00 wt %, the implant may become toxic to tissues and organs in the body. According to literature, use of a great amount of silver leads to Argylia disease (disease leading to graying in color of the entire skin), decrease of leucocytes, and damage to liver and kidney. Our studies also showed that there are deformation of cells and inhibition of neonatal bone formation when the silver concentration is more than 3.00 wt %.

An example of the bioimplant according to the present invention is a synthetic joint consisting of a stem which is a bone contact portion inserted into the bone and a neck unit formed on the top end of the stem for fixation of bone head ball, wherein at least part of the bone contact portion is covered with a thermal spraying film of a calcium phosphate-based material and the silver concentration in the thermal-spray film is 0.05 wt % to 3.00 wt %. The synthetic joint is preferably made of titanium or a titanium alloy.

Examples—Experiment 1 (Sample Preparation)

Hydroxyapatite containing a particular amount of silver oxide was sprayed onto one side of a pure titanium plate with a size of 50 mm×50 mm×2 mm by flame spraying method, to forma thermal-spray film having a thickness of about 40 μm. The flame spraying was carried out by introducing, with 100 psi dry air, the thermal spraying powder into a gas frame torch generated with 50 psi oxygen gas and 43 psi acetylene gas and spraying the fused powder at a thermal spraying distance of 60 to 100 mm.
(Measurement of Silver Concentration)

After sufficient drying at 100° C., each sample was weighed and then dissolved in a nitric acid solution (5 mL of nitric acid and 50 mL of purified water) while heating. The silver concentration in the film was determined by measuring the silver concentration in the solution quantitatively by ICP emission spectrophotometric analysis. Then, the sample after removal of the film by solubilization was dried sufficiently and weighed again, and the film weight was calculated from the difference in weight from the sample before solubilization. The silver concentration in film (wt %) was calculated by dividing the amount of silver in film by the weight of the film. The silver concentration of the film in this experiment was 0.3 wt %.
(Test for Antimicrobial Activity)

As a test for antimicrobial activity, an evaluation of performance of inhibiting biofilm formation was carried out. Methicillin-resistant *Staphylococcus aureus* was adhered to samples, and then the samples was immersed in a fetal bovine serum retained at a temperature of 37° C. and was cultivated under flow condition by stirring at 60 rpm. After culture for one week and two weeks, biofilm formed on the film was stained by fluorescent staining and biofilm coverage on the film was determined and morphology thereof observed by fluorescence microscope. Further, the biofilm coverage was determined from a surface area ratio of a fluorescence emission area obtained by using image analysis software.

Experiment 2

A sample was prepared in a similar manner with experiment 1 except that Hydroxyapatite containing no silver oxide was used, and supplied to the test for antimicrobial activity.
(Result)

Table 1 shows the biofilm coverage. The biofilm coverage of the samples of one-week culture and two-week culture in the experiment 1 became lower than those of the control samples, indicating that the samples of the experiment 1 shows inhibiting the biofilm formation.

TABLE 1

| | Biofilm coverage (%) | |
|---|---|---|
| | After culture for 1 week | After culture for 2 weeks |
| Experiment 1 | 1.3 | 29.9 |
| Experiment 2 | 5.7 | 48.9 |

Experiment 3

This experiment was carried out to reconfirm the effect of the silver concentration in the film, and the samples having silver concentrations of 0, 0.05, 0.1, 0.3 wt % were prepared.
(Sample Preparation)

Hydroxyapatite containing a particular amount of silver oxide was sprayed onto one side of a pure titanium plate with a diameter of 14 mm and a thickness of 1 mm by flame spraying method, to form a thermal-spray film having a thickness of about 40 μm. The samples having silver concentrations of 0, 0.05, 0.1, 0.3 wt % were prepared by adjusting the amount of the silver oxide blended to the thermal spraying material, The flame spraying was carried out in a similar manner as described in Experiment 1.
(Measurement of Silver Concentration)

The measurement of silver concentration was carried out in a similar manner as described in Experiment 1.
Test for Antimicrobial Activity)

As a test for antimicrobial activity, a test of inhibiting biofilm formation was carried out. The test was carried out in a similar manner as described in Experiment 1 except that a culture medium was replaced every fourth day to avoid the culture medium of fetal bovine serum from being saturated with a bacteria.
(Result)

Table 2 shows the results of measurements of the biofilm coverage. The biofilm coverage of the samples of one-week culture and two-week culture in this experiment became lower in proportion to the silver concentration in the film. This indicated that biofilm formation is inhibited as the silver concentration in the film increases. Further, considering the results of this experiment and empirical knowledge on the bacterial growth, it is estimated that the samples maintain an effect of inhibiting biofilm formation for a long period time, such as about four weeks when the silver concentration is 0.05%, about six weeks when the silver concentration is 0.1%, and about ten weeks when the silver concentration is 0.3%.

TABLE 2

| Silver concentration | Biofilm coverage (%) | |
|---|---|---|
| in film (wt %) | After one-week culture | After two-week culture |
| 0 | 28.6 | 55.0 |
| 0.05 | 7.5 | 37.1 |
| 0.1 | 5.3 | 21.4 |
| 0.3 | 3.6 | 9.3 |

Since the bioimplant of the present invention is capable to inhibit the biofilm formation over a long period of time after an operation, the risk of post-operative infection can be significantly decreased. Especially, a large effect can be expected when applying to patients having high risk of infection, for example, to a compromised host or a patient who develops infection after implant operation and have an operation of replacing implant.

The foregoing outlines features of several exemplary embodiments of the invention so that those of ordinary skill in the art may better understand the aspects of the invention. Those skilled in the art will appreciate that they may readily use the present disclosure to make various changes, substitutions, and alterations to the embodiments disclosed herein to arrive at equivalent structures that are encompassed within the scope of the present invention. Thus, the scope of the invention should not be limited by the exemplary embodiments disclosed herein but rather the scope of the invention should be commensurate with the plain meaning of the claims issued from the present disclosure.

What is claimed is:

1. A bioimplant, comprising
a base material of the bioimplant;
a coating film comprising a calcium phosphate-based material and a silver material formed on at least a part of a surface of the base material;
wherein the calcium phosphate-based material comprises oxyapatite and hydroxyapatite, wherein the hydroxyapatite is formed from converting oxyapatite present in the coating into the hydroxyapatite by immersing the coating in deionized water, and
wherein fine crystals of the hydroxyapatite are present on a surface of the coating film, wherein a size of the fine crystals of hydroxyapatite is in a range of 0.01 μm to 2.00 μm in length, thickness or width.

2. The bioimplant according to claim 1, wherein the silver material concentration in the coating film is in a range of 0.05 wt % to 3.00 wt %.

3. The bioimplant according to claim 1, wherein the base material comprises a metal.

4. The bioimplant according to claim 1, wherein the calcium phosphate-based material further comprises a compound or a mixture of two or more compounds selected from the group consisting of alpha-tricalcium phosphate, beta-tricalcium phosphate, and tetracalcium phosphate.

5. The bioimplant according to claim 1, wherein the bioimplant has a bone contact portion, at least part of the bone contact portion is covered with the coating film.

\* \* \* \* \*